United States Patent [19]
Huene

[11] Patent Number: 6,077,267
[45] Date of Patent: Jun. 20, 2000

[54] ABSORBABLE BONE SCREW AND TOOL FOR ITS INSERTION

[76] Inventor: Donald R. Huene, 201 N. Valeria, Fresno, Calif. 93701

[21] Appl. No.: 08/424,067

[22] Filed: Apr. 19, 1995

Related U.S. Application Data

[62] Division of application No. 08/203,764, Mar. 1, 1994, abandoned, which is a continuation of application No. 07/875,262, Apr. 28, 1992, abandoned.

[51] Int. Cl.[7] .............................. A61B 17/86; A61B 17/88
[52] U.S. Cl. ............................. 606/73; 81/437; 411/405; 411/919; 606/77; 606/104
[58] Field of Search .................................. 606/72, 73, 77, 606/104; 411/405, 407, 410, 919; 81/437, 90

[56] References Cited

U.S. PATENT DOCUMENTS

| | | | |
|---|---|---|---|
| 1,007,107 | 10/1911 | Hulsmann | 606/104 |
| 1,300,275 | 4/1919 | Johnson | 411/407 |
| 2,180,633 | 11/1939 | Holt | 85/45 |
| 2,267,925 | 12/1941 | Johnston | 411/407 |
| 2,347,567 | 4/1944 | Kreese | 32/12 |
| 3,695,321 | 10/1972 | Garehime, Jr. | 145/50 |
| 4,018,111 | 4/1977 | Goldhaber | 81/71 |
| 4,057,890 | 11/1977 | Feen | 29/427 |
| 4,466,314 | 8/1984 | Rich | 81/90 C |
| 4,466,315 | 8/1984 | Boschetto et al. | 81/437 |

FOREIGN PATENT DOCUMENTS 320791  6/1989  European Pat. Off. .

OTHER PUBLICATIONS

Orthopaedic Review, vol. VII, No. 1, Jan. 1978, Donald R. Huene.

*Primary Examiner*—Danton D. DeMille
*Attorney, Agent, or Firm*—Liniak, Berenato, Longacre & White, LLC

[57] ABSTRACT

A bone screw comprises a threaded shank having an axis of rotation. A head is integral with the shank, and the head includes a surface disposed generally normal to the axis. A plurality of drive receivers are disposed about the surface wholly remote from the axis. Each of the drive receivers is adapted for engagement with a cooperating driver element of a rotary driver so that the head and thereby the shank may be rotated about the axis.

8 Claims, 2 Drawing Sheets

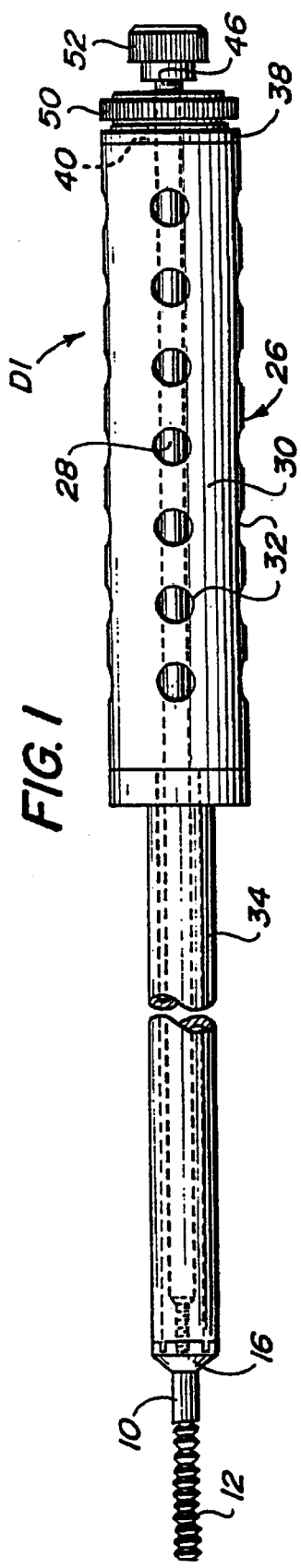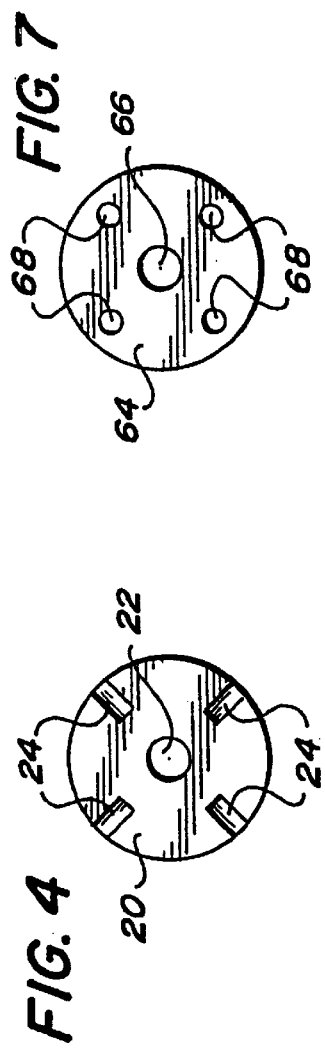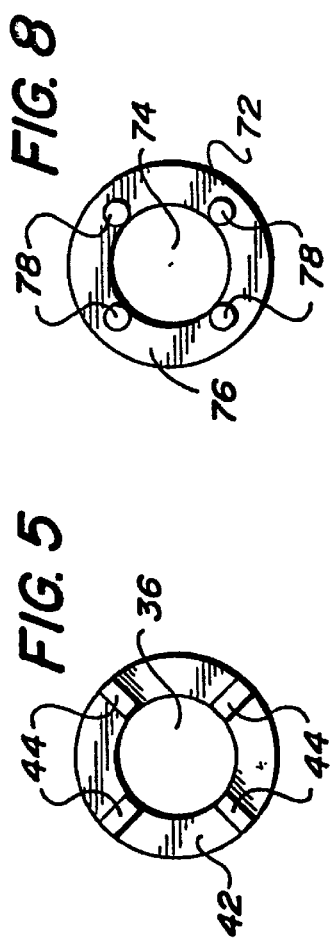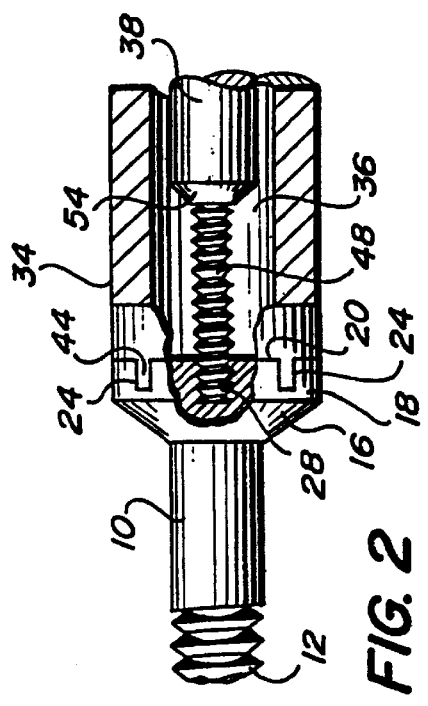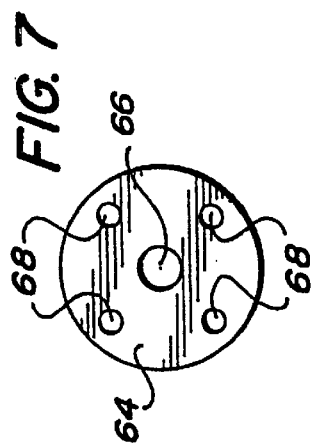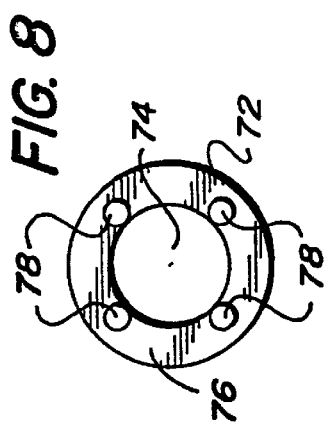

ABSORBABLE BONE SCREW AND TOOL FOR ITS INSERTION

This is a division of application Ser. No. 08/203,764 filed Mar. 1, 1994, now abandoned, which is a continuation of application Ser. No. 07/875,262 filed on Apr. 28, 1992, now abandoned.

FIELD OF THE INVENTION

The disclosed invention is a screw for the internal fixation of bone fragments. The screw is manufactured from a material which is absorbable by the body into which the screw is to be inserted. A tool to which the screw may be selectively fixed is also disclosed, and the tool maintains proper orientation and alignment of the screw throughout the insertion process.

BACKGROUND OF THE INVENTION

The internal fixation of bone fragments through the utilization of bone screws is well known. The screws may be manufactured from metal, but metal screws may need to be removed after the fragments have knitted. Absorbable materials have recently been developed for various medical applications, including for the fixation of bone fragments. Absorbable materials avoid the need for removal of the bone screw at a subsequent date, thereby eliminating the need for additional surgery.

Because the bone screw is screwed into the fragments in order to fix them, there is a need for a tool which rotates the screw about its longitudinal axis. Placement of the bone screw may require great accuracy, and various devices have been proposed for fixing a bone screw relative to its cooperating driver. Absorbable bone screws, however, generally are formed from materials not having the strength characteristics of metal, so that prior surgical screwdrivers may not maintain proper orientation of the screw relative to the driver. The absorbable screw may, for example, become cocked or knocked off axis during insertion, with the result that the screw may not be properly inserted. In addition, the surgeon may not have a clear view of the screw during the entire installation process, because the view may be blocked by tissue, blood or the like, so as to be unaware that the screw has not been properly positioned.

In view of the above, those skilled in the art will understand that there is a need for an absorbable bone screw and a tool for its insertion which assure proper positioning of the screw relative to the driver at all times. The disclosed invention is thus directed to a unique absorbable bone screw, and a tool especially adapted for insertion of that bone screw.

OBJECTS AND SUMMARY OF THE INVENTION

The primary object of the disclosed invention is an absorbable bone screw which cooperates with a driver for maintaining proper orientation of the screw relative to the driver.

A bone screw, according to the invention, comprises a threaded shank having an axis of rotation. A head is integral with the shank, and the head includes a surface disposed generally normal to the axis of the shank. A plurality of driver means are disposed about the surface wholly remote from the axis. Each of the driver means is adapted for engagement with a cooperating driver element of a rotary driver, so that the head and thereby the shank may be rotated about the axis.

A bone screw comprises a shank threaded along a portion thereof, and the shank has an axis of rotation. A head is integral with the shank. The head includes a flaring portion extending from the shank and a cylindrical portion extending from the flaring portion and terminating in a surface generally normal to the axis. The head and the shank are formed from a material absorbable by the body into which the screw is to be inserted. A threaded bore is formed in the head coaxial with the axis, and the bore extends at least to the flaring portion. A plurality of driver means are formed in the cylindrical portion and open on the surface. The driver means are equiangularly disposed about the surface and are wholly remote from the bore.

A driver for a bone screw, according to the invention, comprises an outer member having a handle portion, with a closed end and an aperture therethrough, and a coaxial tube portion extending therefrom. A plurality of driver elements are equiangularly disposed about and extend from the tube portion parallel to the axis thereof. A rod member is threaded at opposite ends thereof. One of the threaded ends extends through and from the tube portion remote from the driver elements, and the other one of the threaded ends extends through and from the closed end. A nut is threadedly engaged with the other one of the threaded ends and is engageable with the closed end so that, after a bone screw has been threaded onto the one threaded end and engaged with the driver elements, the nut may be rotated into engagement with the closed end for thereby displacing the rod member and causing the screw to be firmly secured to the tube portion.

These and other objects and advantages of the invention will be readily apparent in view of the following description and drawings of the above described invention.

DESCRIPTION OF THE DRAWINGS

The above and other objects and advantages and novel features of the present invention will become apparent in the following detailed description of the preferred embodiment of the invention illustrated in the accompanying drawings, wherein:

FIG. 1 is an elevational view, with portions shown in phantom and with broken lines indicating indefinite length, of a bone screw of the invention attached to a driver of the invention;

FIG. 2 is an enlarged fragmentary elevational view, partially in section, of the bone screw and driver of FIG. 1;

FIG. 4 is a top plan view of the bone screw of FIG. 3;

FIG. 5 is a bottom plan view of the screw driver of FIG. 3;

FIG. 7 is a top plan view of the bone screw of FIG. 6; and

FIG. 8 is a bottom plan view of the driver of FIG. 6.

DESCRIPTION OF THE INVENTION

Figure 3:
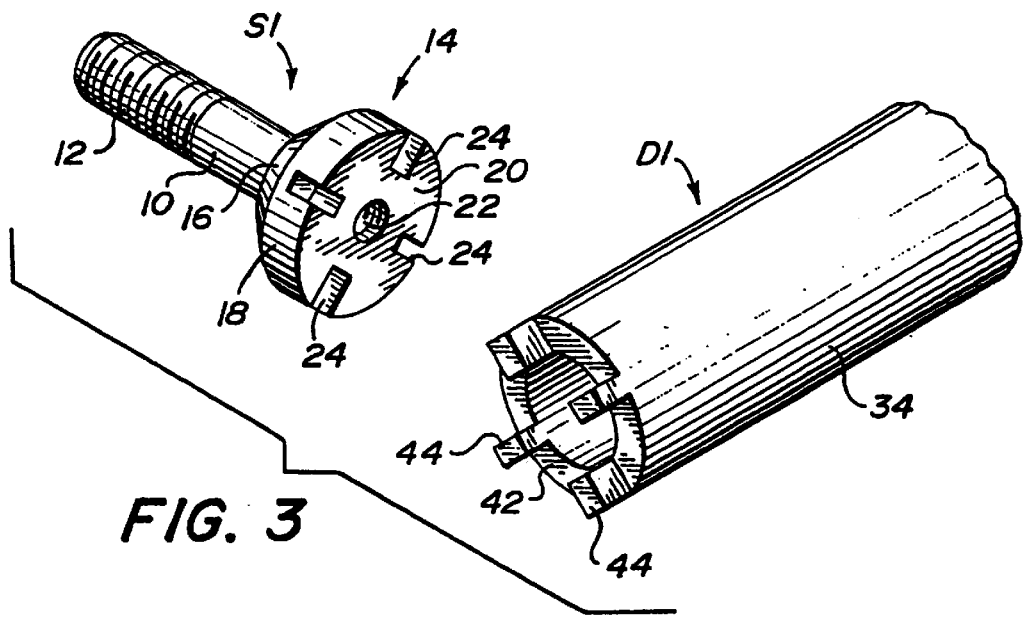
FIG. 3 is an exploded assembly drawing of a first embodiment of a bone screw and a portion of the first embodiment of the driver of FIG. 2.

Bone screw S1, as best shown in FIG. 3, has a shank 10 and a plurality of threads 12. The threads 12 extend only along a portion of the length of shank 10, and the screw S1 is thus a compression screw. Screw S1 has a head 14 formed by outwardly flaring portion 16 and cylindrical portion 18 extending therefrom. Head 14 is integral with shank 10, and is coaxial therewith as would be understood by those skilled in the art. Cylindrical portion 18 terminates in a flat surface 20 which is normal to the longitudinal axis of the shank 10.

Bone screw S1 is manufactured from a material which is absorbable by the body into which the screw S1 is to be inserted for fixing bone fragments. I prefer that the screw S1 be manufactured from Orthosorb, sold by Johnson & Johnson, although various other absorbable materials may be used. Orthosorb is a rigid, non-inflammatory, non-allergic material which can withstand the functional stress to which screw S1 is to be put. The material should meet Brunetti's criteria. Poly-P-dioxanone is such a material. It is known, for example, to manufacture absorbable surgical products from polymers or copolymers of glycolic and lactic acids. Regardless of the material used, it is generally not as rigid and strong as metal, and has a very soft hardness, probably on the order of a Rockwell hardness of 2 or 3.

Bone screw S1 has a central threaded bore 22, as best shown in FIGS. 2 and 3. Bore 22 is coaxial with shank 10. The threads about the circumference of bore 22 are a number 4–40 NC thread. Although other thread sizes may be used, I have found that this threading provides adequate fixation of the bone screw S1. Bore 22 preferably extends within head 14 to flaring portion 16.

As best shown in FIGS. 2–4, a plurality of equiangularly disposed generally rectangular slots 24 are formed in cylindrical portion 18 of head 14. Each of the slots 24 is wholly remote from the bore 22, and each slot 24 opens on the surface 20 and on the outer periphery of cylindrical portion 18. Slots 24, as best shown in FIG. 2, extend into the cylindrical portion 18 to a point remote from flaring portion 26. Slots 24 thus terminate in head 14 at a point vertically spaced from the point of termination of bore 22. While I show slots 24 formed into head 14, those skilled in the art will understand that these driver means could extend outwardly from the head. I prefer that they extend into the head in order to minimize protusions.

Driver D1, as best shown in FIGS. 1–3, is manufactured from a surgical grade of stainless steel. Driver D1 has a first tubular member 26 and a rod member 28 disposed therein. Tubular member 26 includes an upper handle portion 30 with a plurality of apertures 32 communicating with the central bore thereof. Tube member 34 is integral with handle portion 30 and has a central aperture 36, as best shown in FIG. 5, coaxial with handle portion 30 and its internal bone. Handle portion 30 is closed at its upper end 38 by a cap or the like, and has a central aperture 40 coaxial with aperture 36 of tube member 34. Handle portion 30 has a diameter exceeding the diameter of tube member 34, in order to fit the hand of the surgeon while minimizing the size of tube member 24 and the incision required for its access.

Tube member 34, as best shown in FIG. 3, has an end surface 42 from which integral rectangular keys 44 extend. The keys 44 are equiangularly disposed about tube 34, and there is a key 44 for each of the slots 24. The keys 44 are sized and configured to be received within the slots 24. Each of the keys 44 extends between the inner and outer walls of tube member 34, and thereby do not block the aperture 36. The keys 44 thus have relatively substantial strength, and may therefore apply the torque required to insert screw S1 into the bone fragments.

Rod member 28, as best shown in FIGS. 1 and 2, has threads 46 at its upper end, and threads 48 at its lower end. The threads 46 pass through the aperture 40 of closed end 38, and a knurled nut 50 is threadedly engaged with the threads 46. Knurled handle 52 is secured to rod member 28 above threads 46 and nut 50, and handle 52 may rotate the rod member 28 on its longitudinal axis.

As noted, rod member 28 extends through aperture 40 in closed end 38 and through the aperture 36 of tube member 34. The threads 48 at the end of rod member 28 correspond to the threads within the bore 22, so that the end of the rod member 28 may be threaded into and out of the bore 22. Rod member 28 has a flaring portion 54 connecting the cylindrical portion thereof to the threaded portion at 48. Rod member 28 has a diameter less than the diameter of bore or aperture 36 in order to permit easy displacement of rod member 38 as the screw S1 is being attached and detached.

Use of the driver D1 for installation of a bone screw S1 is relatively simple and straightforward. The screw S1 may be relatively rapidly inserted into the bone fragments (not shown), and then may be just as quickly detached from the driver D1 in order to permit the surgical procedure to continue.

Nut 50 is initially threaded about the threads 46 in order to be closely proximate handle 52. The rod member 28 is then inserted through the apertures 40 and 36, with the result that the threads 48 extend through the aperture 36 and beyond the end 42 and the keys 44. The bore 22 of the screw S1 is threaded onto the threads 48, and then rod member 28 is displaced within tubular member 26 and keys 44 aligned with slots 24. The keys 44 are received within the slots 24, and then the nut 50 is rotated in the opposite direction about the threads 46 in order to engage closed end 38. Engagement of nut 50 with closed end 38 causes the rod member 28 to be moved within the tubular member 26, and thus handle 52 moved further outwardly, so that the surface 20 of bone screw S1 becomes tightly engaged with the end surface 42 of tube member 34 between keys 44. Continued rotation of nut 50 will increase the tension fixing screw S1 to driver D1. The tension will not strip the threaded connection of rod member 28 from bore 22 because of the number and configuration of the threads 48 and the corresponding threads within bore 22. The tension on screw S1 is sufficient to prevent the screw from cocking or otherwise being moved off axis as the screw is inserted into the bone fragments. The screw S1 is thus coaxially aligned with the axis of rotation of the rod member 28 and with the tubular member 26, and is tightly engaged because of the threaded attachment of the threads 48 within the bore 22 and the tension applied by rod member 28 and nut 50. The screw S1 may thus be rotated as is conventional in order to secure the fragments (not shown) together.

Once the bone fragments (not shown) have been secured together by rotation of the screw S1 about its longitudinal axis, then the driver D1 may be rapidly disengaged from the screw S1 in order to permit the surgical procedure to continue. The surgeon need merely rotate the nut 50 about the threads 46 in order to cause the nut 50 to approach the handle 52. Movement of the nut 50 thus releases the tension on the screw S1, and permits the tubular member 26 to be moved relative to the now fixed screw S1. The nut 50 is rotated by an amount sufficient to permit the keys 44 to be removed from the slots 24 and spaced from the surface 20. The handle 52 may then be rotated in order to detach the threads 48 from the bore 22.

Figure 6:
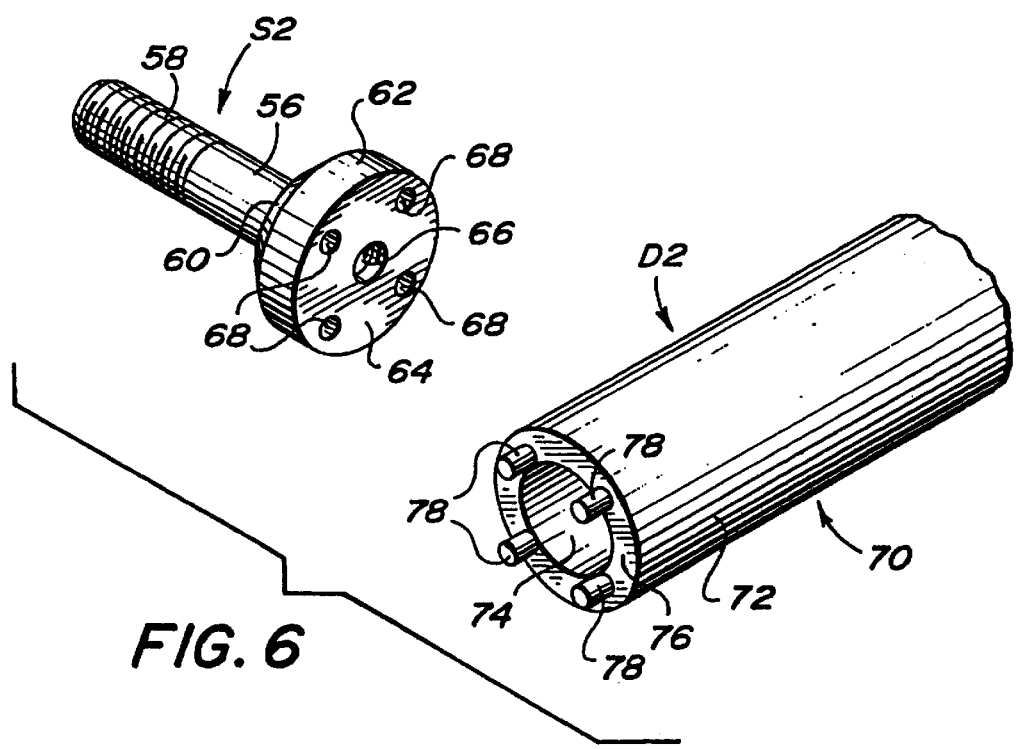
FIG. 6 is an exploded assembly drawing of a second embodiment of a bone screw and a second embodiment of a portion of a screwdriver according to the invention.

Screw S2 of FIGS. 6–8 is similar to the screw S1 of FIGS. 1–3, and is comprised of a bioabsorbable material for like reasons. The driver D2 is substantially similar to the driver D1 of FIG. 1, and thus I will only elaborate on the differences.

Screw S2 has a shank 56 with threads 58 extending along a portion of the length thereof. The screw S2 is also a compression screw, although other screw types are available. As with the screw S1, screw S2 has a flaring portion 60 coaxial with shank 56 and integral cylindrical portion 62. Cylindrical portion 62 has a flat surface 64 which is normal to the axis of rotation of the shank 56.

As with bone screw S1, a central bore 66 is formed in cylindrical portion 62 and terminates at flaring portion 60. The bore 66 is threaded with the same sorts of threads formed in the bore 22.

Unlike the bone screw S1, bone screw S2 has a plurality of cylindrical detents 68 formed in cylindrical portion 62. Each of the detents 68 is wholly remote from the bore 66, and is also inwardly spaced from and wholly remote from the periphery of cylindrical portion 62. The detents 68 each open on the surface 64, and each detent extends into the cylindrical portion 62 in order to terminate short of flaring portion 60. Bore 66 thus extends beyond the detents 68.

The tubular member 70 of the driver D2, which corresponds to the tubular member 34 of the driver D1, has a cylindrical outer surface 72 and a central cylindrical bore 74. The tubular member 70 terminates in a flat surface 76 extending generally transverse to the axis defined by the bore 74. A plurality of cylindrical posts 78 extend from the surface 76, and there is a post 78 for each of the detents 68. Unlike the keys 44, each of the post 78 is substantially disposed between the bore 74 and the outer wall 72, such that the diameter of each post 78 is less than the thickness of the wall of tubular member 70.

Use of the screw S2 with the screwdriver D2 is substantially the same as for the screw S1 and the screwdriver D1, as those skilled in the art will understand. As with the screwdriver D1, the screwdriver D2 firmly secures the screw S2 during insertion in order to maintain coaxial alignment of the screw S2 relative to the driver D2. The threads about the bore 66 are such as to substantially prevent the screw S2 from being stripped from the cooperating threads on the rod member of the driver D2, and the plastic-like nature of the material from which the screws S1 and S2 are manufactured facilitates engagement and disengagement by the threaded end of the rod member.

I have found it important to make certain that the slots 24 and the detents 68 are wholly remote from the central bores 22 and 66, respectively. Because the slots 24 and detents 68 are wholly remote from their center bore, then I can utilize substantially all of the longitudinal thickness of the head of the screw for engagement with the threads on the rod member. Conventional screws, whether straight blade or of the Phillips type, always have some portion of the head removed at the intersection with the axis of rotation, so that the removed material is not available for threading. Those skilled in the art will understand that the fewer the threads, then the less the holding power. Should some portion of the head not be available for threading, then the central bore must extend further into the screw shank in order to provide sufficient threads for a good hold. It is undesirable, however, to bore into the shank of the screw, because the shank has a diameter less than the diameter of the head and the wall thickness of the shank will therefore be decreased, possibly permitting the head to be severed from the shank or else necessitating that the shank be larger in diameter. The larger the diameter of the shank, however, then the larger the hole into which the screw is to be inserted and thus the larger the bone fragments must be.

While this invention has been described as having a preferred design, it is understood it is capable of further modifications, uses and/or adaptations of the invention, following in general the principle of the invention and including such departures from the present disclosure has come within known or customary practice in the art to which the invention pertains, and as may be applied to the central features here and before set forth, and fall within the scope of the invention of the limits of the appended claims.

What I claim is:

1. A driver for an absorbable bone screw, comprising:
   a) an apertured outer member including a handle portion with a closed end and a coaxial open tube portion extending from said handle portion, said tube portion having inner and outer tube walls;
   b) a plurality of driver elements equiangularly disposed about and extending from said tube portion parallel to the longitudinal axis, each driver element being wholly disposed between said inner and outer tube walls and not extending into the opening of said tube portion;
   c) a rod member threaded at opposite ends thereof, one of said threaded ends extending through and from said tube portion remote from said driver elements and the other of said threaded ends extending through and from said closed end; and
   d) a nut threadedly engaged with said other one threaded end and engageable with said closed end so that, after an absorbable bone screw has been threaded onto said one threaded end and has received said driver elements, said nut may be rotated into engagement with said closed end for thereby displacing said rod member and causing the screw to be firmly secured to said tube portion.

2. The driver of claim 1, wherein:
   a) each of said driver elements is one of a rectangular key and a cylindrical post.

3. The driver of claim 1, wherein:
   a) each of said driver elements is a rectangular key.

4. The driver of claim 3, wherein:
   a) each of said keys spans said tubular portion between the inner and outer peripheries thereof.

5. The driver of claim 1, wherein:
   a) each of said driver elements is a cylindrical post.

6. The driver of claim 5, wherein:
   a) each of said posts is disposed intermediate the inner and outer peripheries of said tubular portion.

7. The driver of claim 1, wherein:
   a) said tube portion opening has a diameter substantially in excess of a diameter of said rod member so that said driver elements are spaced from said one threaded end.

8. The driver of claim 7, wherein:
   a) there are at least four driver elements.

* * * * *